United States Patent [19]

Arts et al.

[11] 4,092,860

[45] June 6, 1978

[54] LEVEL MEASUREMENT AND CONTROL

[76] Inventors: Matheus Gijsbertus Jozef Arts, Burgemeester Mollaan 5, Waalre; Jozef Augustinus Elisabeth Spaan, Esdoornstraat 2, Nuenen; Antonius Gerardus Martinus v. Asseldonk, Outshoornstraat 33; Johannes Augustinus Catharinus Maria de Maat, Cassandraplein 19, both of Eindhoven, all of Netherlands

[21] Appl. No.: 622,398

[22] Filed: Oct. 14, 1975

[30] Foreign Application Priority Data

Oct. 14, 1974 Netherlands .................. 7413475

[51] Int. Cl.² ............................................ G01F 23/24
[52] U.S. Cl. .............................................. 73/304 R
[58] Field of Search .................... 73/304 R, 304 C; 137/392; 128/1 D, 2.05 R

[56] References Cited

U.S. PATENT DOCUMENTS

| 3,772,531 | 11/1973 | Webb et al. | 137/392 |
| 3,848,616 | 7/1972 | Sanner | 137/392 |
| 4,010,650 | 3/1977 | Piatkowski | 73/304 C |

*Primary Examiner*—Donald O. Woodiel
*Attorney, Agent, or Firm*—Haseltine, Lake & Waters

[57] ABSTRACT

Method and arrangement for measuring and controlling the level of a fluid in a container. The conductivity of the fluid is measured by means of a detector and a high-frequency voltage supply. The detector operates on a capacitive or on an inductive basis. Means for eliminating the effect of the size of the container and of the transfer functions of the detector and, in the control arrangement, the pump.

10 Claims, 9 Drawing Figures

LEVEL MEASUREMENT AND CONTROL

BACKGROUND OF THE INVENTION

The present invention relates to a method and arrangement for measuring the level of a fluid or other suitable substance contained in a container, as well as to a method and arrangement for controlling the level of a fluid or other suitable substance contained in a container.

Such methods and arrangements may be used in many fields concerned with the sucking-off or delivery of a fluid or other suitable substance, especially in the level measurement and/or control associated with extracorporal blood circulation.

The methods and arrangements described hereinafter are particularly suited for use in the medical field, but the principle described may also be used to advantage in other fields, notably when the level of a fluid or particulate mass contained in a natural or artificial container is to be measured and/or controlled.

In the medical field, surgical operations often require the blood to be sucked out of a wound. An example thereof is the so-called open-heart surgery. The blood is sucked out of the wound (heart) by means of a suction nozzle and is subsequently extracorporally circulated through an appropriate apparatus, during which circulation the blood may be subjected to a certain treatment, and is finally re-introduced into the body.

It is vital that no air bubbles are formed during sucking. The suction nozzle should therefore extend into a puddle of blood during the entire sucking operation. Moreover, to prevent blood damage, the sucking may not be performed at a too high acceleration. Furthermore, direct contact between electrodes and blood or tissue is often undesirable.

It is an object of the present invention to provide a method based on the concept of capacitive or inductive measurement of the conductivity of the fluid or other substance, which method solves the above problems.

SUMMARY OF THE INVENTION

The objects of the present invention are achieved by providing in accordance with one embodiment of the present invention, a method of measuring the level of a fluid or other suitable substance contained in a container. A detector including at least two electrodes insulated from the fluid or substance is immersed in the fluid or substance, the electrode being coupled to a high-frequency voltage supply. The conductivity of the fluid or substance between the electrodes is measured at a frequency such that the capacitance between each electrode and the fluid or substance is negligible.

In accordance with another embodiment of the idea underlying the present invention, a method of measuring the level of a fluid or other suitable substance contained in a container has the feature that a detector including a hollow coil insulated from the fluid or substance is immersed in the fluid or substance. A capacitor is connected parallel to the coil and the coil is coupled to an a-c voltage supply producing a voltage having a frequency equal to the resonant frequency of the LC circuit formed. The impedance of the LC circuit is measured at this frequency.

In accordance with a practical embodiment of the idea underlying the present invention, an arrangement for performing the above methods has the feature of a detector adapted to be immersed in the fluid or substance, the detector including at least two electrodes insulated from the fluid or substance. One of the electrodes is connected to one terminal of a high-frequency voltage supply and the other of the electrodes to one terminal of a load resistor having its other terminal connected to the other terminal of the high-frequency voltage supply. A detector may be adapted to immersion in the fluid or substance. The detector includes a hollow coil insulated from the fluid or substance, and a capacitor is connected parallel to the coil. One junction of the resultant LC circuit is connected to one terminal of an a-c voltage supply adapted to produce a voltage having a frequency equal to the resonant frequency of the LC circuit. The other junction of the LC circuit is connected to one terminal of a load resistor having its other terminal connected to the other terminal of the a-c voltage supply.

Furthermore, in accordance with the present invention, a method of controlling the level of a fluid or other suitable substance contained in a container has the feature that a suction or delivery nozzle, which is connected to a pump and includes at least one set of electrodes, is immersed in the fluid or substance. There is no direct contact between the electrodes on the one hand and the fluid or substance and the container on the other hand. A voltage proportional to the conductivity of the fluid or substance between the electrodes is formed by means of a high-frequency measuring voltage and is multiplied by the measuring voltage in a synchronous detector. The output voltage of the detector is measured and used to control the pump so that a presettable level is maintained. A suction or delivery nozzle, may instead, be connected to a pump and include a hollow coil having a capacitor connected parallel thereto. The nozzle is immersed in the fluid or substance. There is no direct contact between the coil on the one hand and the fluid or substance and the container on the other hand. A voltage proportional to the conductivity of the fluid or substance within the hollow coil is formed by means of a high-frequency measuring voltage and is multiplied by the measuring voltage in a synchronous detector. The output voltage of the detector is measured and used to control the pump so that a presettable level is maintained.

BRIEF DESCRIPTION OF THE DRAWINGS

The present invention will be described in detail hereinafter with reference to the accompanying drawings, in which.

DESCRIPTION OF THE PREFERRED EMBODIMENTS

Figure 1:
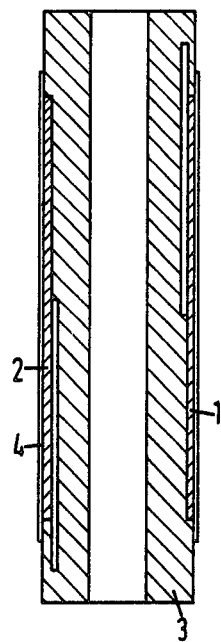
FIG. 1 shows a cross-section of an embodiment of a detector cum suction nozzle according to the present invention including electrodes.

Reference is made to FIG. 1. This figure shows in cross-section an embodiment of a detector for level measurement according to the invention. For level control applications, this detector has the form of a suction nozzle (as shown), comprising two groups of a number of electrodes 1, 2, for example copper strips. These electrodes are embedded in a suction nozzle 3 of plastics material and are fully covered by a teflon membrane 4 having a thickness of 8 microns in the embodiment described.

Figure 2:
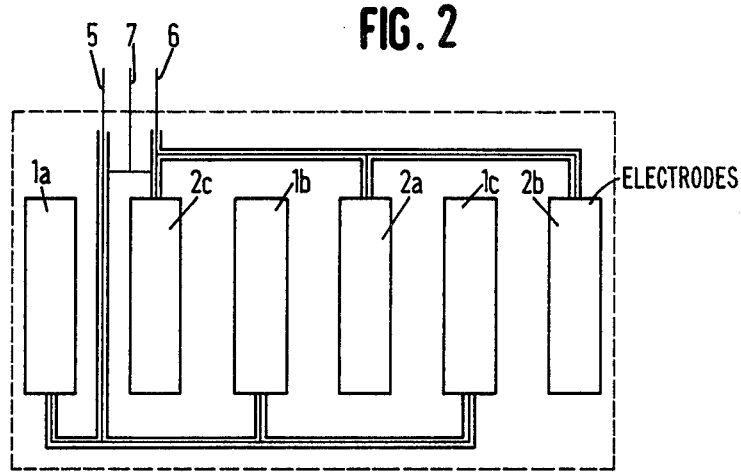
FIG. 2 shows the suction nozzle according to FIG. 1 developed in the plane of the drawing.

FIG. 2 shows a detector cum suction nozzle (developed in the plane of the drawing) having a total number of six electrodes 1a, 1b, 1c and 2a, 2b, 2c. Electrodes 1a, 1b, 1c are interconnected through an insulated wire 5 and electrodes 2a, 2b, 2c are interconnected through an insulated wire 6. Although this FIG. 2 shows a configuration having alternating electrodes, this is not essential for the present invention. In principle, the presence of two electrodes contacting the same fluid suffices.

Figure 4:
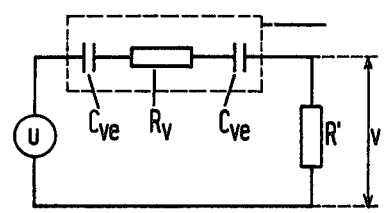
FIG. 4 shows a replacement diagram of the assembly of two electrodes of the suction nozzle immersed in a fluid.

Such a configuration may be represented by the replacement diagram shown in FIG. 4. This diagram also includes a voltage supply U and a load resistor R'. $C_{ve}$ is the capacitance between the fluid into which the nozzle extends and one of the electrodes, $R_v$ is the resistance of the fluid between two electrodes.

It will be clear that the resistance $R_v$ and the capacitances $C_{ve}$ depend on the nature of the fluid and the membrane as well as on the height of the fluid between the electrodes. Resistance $R_v$ may be represented by the formula $R_v = a/h$, in which $a$ is a constant and $h$ is the height of the fluid between the electrodes. The value of the capacitances $C_{ve}$ is proportional to $h$, so that a constant RC product is obtained and thus a constant phase is obtained when measuring $h$.

In order to measure $h$, the value $R_v$ is measured by means of a high-frequency voltage U. The frequency of the voltage U is selected so that the influence of capacitances $C_{ve}$ is negligible. With $C_{ve}$ negligible, there is a linear relationship between the potential V across the resistor R', which potential is to be measured, and the value $1/R_v$. As $R_v$ is proportional to $1/h$, V will also be proportional to $h$. Consequently, V is a measure for the height of the fluid between the electrodes.

By arranging the electrodes in alternating fashion around the suction aperture of the nozzle, the effect of the angle between the axis of the suction nozzle (detector) and the fluid level as well as the effect of rotations about this axis will be eliminated.

Figure 3:
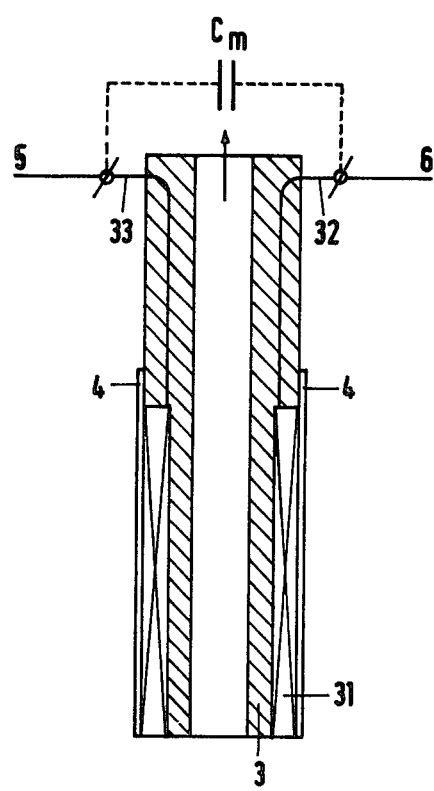
FIG. 3 shows a suction nozzle according to the present invention including a coil.
Figure 5:
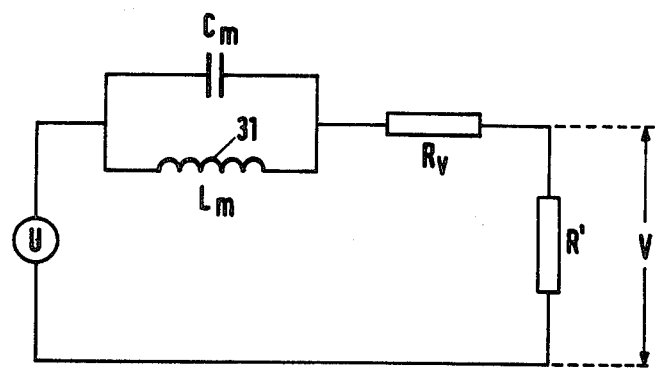
FIG. 5 shows the replacement diagram associated with the nozzle according to FIG. 3.

In addition to the capacitive measurement by means of one or more sets of electrodes, the level of a fluid or other suitable substance contained in a container may also be determined by an inductive measurement. FIG. 3 shows a detector designed for this purpose including an embedded hollow coil 31 covered by a membrane 4. The detector is arranged so that use as suction or delivery nozzle is feasible. The coil includes lead wires 32, 33 partly embedded in the nozzle. For performing the inductive measurement of $R_v$, a capacitor $C_m$ is connected parallel to the coil 31. The frequency of the high-frequency voltage is selected equal to the resonant frequency of the circuit $L_mC_m$ (FIG. 5), so that the influence of $L_m$ and $C_m$ is negligible and V is again proportional to the height of the fluid within the hollow coil.

Figure 6:
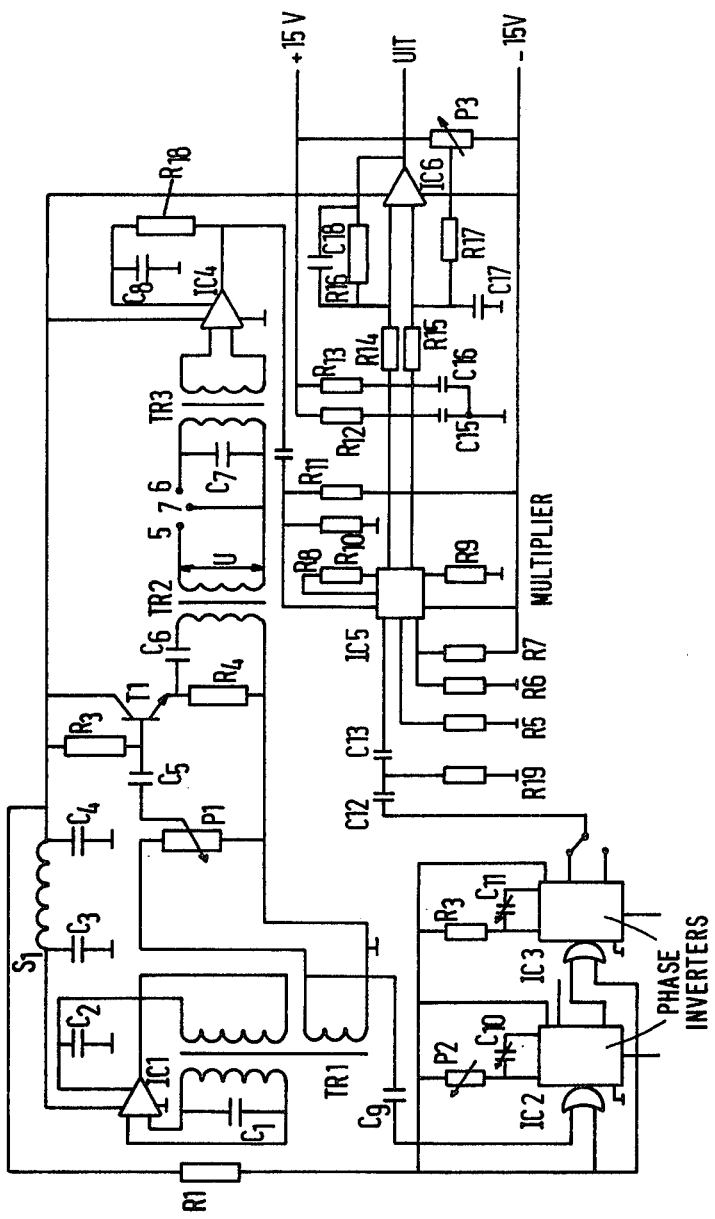
FIG. 6 schematically shows a level detection circuit arrangement according to the present invention.

FIG. 6 shows schematically a level detection circuit arrangement adapted to cooperate with the detector shown in FIG. 1 or FIG. 3. The arrangement shown comprises an integrated operational amplifier $IC_1$ serving as an oscillator having a frequency of 4 MHz. The output signal of operational amplifier $IC_1$ is applied through a transformer $TR_1$ to a transistor $T_1$ connected in emitter-follower configuration. The output signal of the emitter-follower is applied to the primary side of a transformer $TR_2$, resulting in the generation of the measuring voltage U (FIGS. 4, 5) on the secondary side of $TR_2$.

The lead terminals 5, 6, 7 of the detector are connected between the secondary side of transformer $TR_2$ and the primary side of a transformer $TR_3$. For considerations of safety, the detector is floatingly connected to the rest of the circuit arrangement in this manner.

The secondary side of $TR_3$ is connected to the input of a high-frequency amplifier constituted by integrated circuit $IC_4$. The output signal of the high-frequency amplifier is applied to a synchronous detector constituted by integrated multiplier circuit $IC_5$. To this synchronous detector there is also applied the output signal of a phase inverter constituted by two integrated circuits $IC_2$ and $IC_3$. The output signal of the oscillator is applied to the input of the phase inverter. The phase inverter serves to compensate for phase inversion of the measuring signal so as to permit detection by means of the synchronous detector.

The outputs of the synchronous detector are connected through resistors $R_{14}$ and $R_{15}$ respectively to the inputs of an operational amplifier $IC_6$ connected as P-controller. A desired level can be set by means of a potentiometer $P_3$ connected between the positive and negative supply leads of $IC_5$ and $IC_6$, which potentiometer has its slider connected to one input of $IC_6$.

Figure 7:
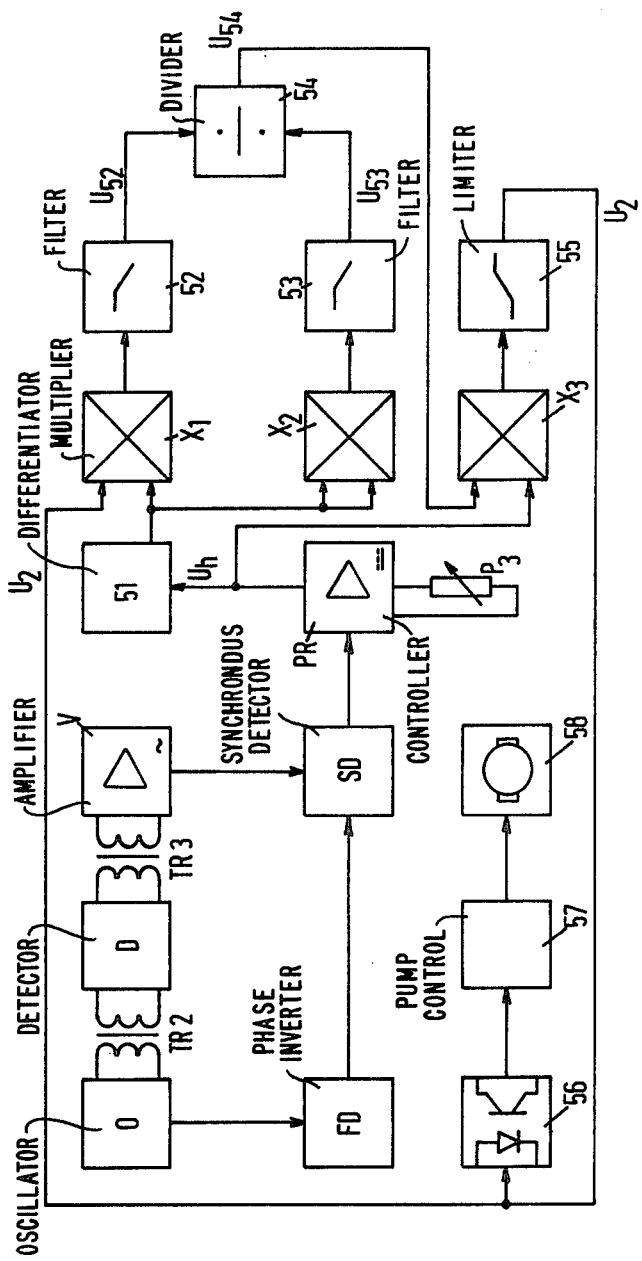
FIG. 7 shows a block diagram of a control arrangement with suction system according to the invention.

FIG. 7 shows a block diagram of the level control arrangement according to the invention. This arrangement includes the level detection circuit arrangement shown in detail in FIG. 6, the oscillator being designated by block O, the detector by D, the high-frequency amplifier by V, the phase inverter by FD, the synchronous detector by SD and the P-controller by PR.

FIG. 7 further shows a circuit arrangement adapted to effect an automatic correction for the surface area of the fluid to be sucked off. This part of the arrangement includes a differentiator 51, three multipliers $X_1$, $X_2$, $X_3$, two low-pass filters 52, 53 connected to the outputs of $X_1$ and $X_2$ respectively, a divider 54 to which the output signals of filters 52, 53 are applied, and an acceleration limiter 55 serving to limit over- or underpressure occurring during sucking. FIG. 7 also show three interconnected blocks 56, 57, 58 representing an optical coupling, a pump control and a pump respectively, which will be described in detail hereinafter.

First the automatic surface area correction will be described.

Figure 8:
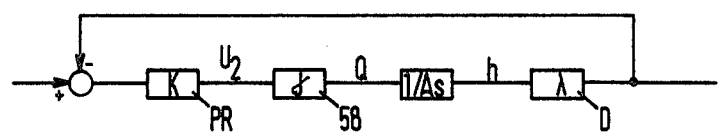
FIG. 8 shows a block diagram of a portion of the arrangement according to the invention.

Reference is made to FIGS. 7 and 8. FIG. 8 shows a block diagram of the arrangement without automatic surface area correction. The relationship between the sucked amount Q the height $h$ of the fluid is represented by the formula: $Q = A (dh/dt)$ (1), in which A is the surface area, i.e. the size of the wound.

In accordance with Laplace, $Q(s) = A \, s \, h(s)$, in which $s$ is the Laplace operator.

Re-arrangement of this equation leads to:

$$\frac{h(s)}{Q(s)} = \frac{1}{As}. \quad (2)$$

$1/As$ may be regarded the transfer function of the wound. The open loop gain in the diagram shown in FIG. 8 will then be $K\gamma(1/As) \lambda$, in which K is the transfer function of the P-controller PR, $\gamma$ is the transfer function of the pump and $\lambda$ is the transfer function of the detector.

In order to make the loop gain independent of A, the following procedure is followed. It follows from (1) that:

$$A = \frac{\Delta Q}{\Delta \frac{dh}{dt}} \quad (3)$$

Information as regards $\Delta$ h follows from $U_h$, which is the output voltage of PR (FIG. 7). Information as regards $\Delta$ Q follows from $U_2$, which is the control voltage for the pump. Suppose that $U_2 = U_{20} \sin \omega t$ (4) and $$dU_h/dt = P(t) = P_o \sin (\omega t + \varphi) \quad (5).$$

Multiplication of (4) by (5) produces, after a low-pass filter has been passed, a voltage $U_{52} = \frac{1}{2} U_{20} P_o \cos \sigma$ (6). Multiplication of (5) by itself produces, after a low-pass filter has been passed, a voltage $U_{53} = \frac{1}{2} P_o^2$ (7). Division of (6) by (7) produces the function $$\frac{\frac{1}{2} U_{20} P_o \cos \varphi}{\frac{1}{2} P_o^2} = \frac{U_{20}}{P_o} \cos \varphi = \frac{\frac{Q}{\gamma} \cos \varphi}{\lambda \frac{dh}{dt}} = \frac{A}{\lambda \gamma} \cos \varphi. \quad (8)$$

When this function is multiplied by the original transfer function $K\gamma\lambda/As$, A as well as $\gamma$ and $\lambda$ are eliminated.

Consequently, the surface area and the transfer functions of the pump 58 and the detector have no effect on the overall level control.

The above is realized as shown in FIG. 7, in which the output voltage $U_h$ of the P-controller is applied to the differentiator 51. The latter is arranged to supply an output voltage $dU_h/dt$ to a multiplier $X_1$, to which also the pump control voltage $U_2$ is applied. The output of the multiplier $X_1$ is connected to a low-pass filter 52, which is arranged to produce an output voltage $U_{52}$ represented by formula (6).

The voltage $dU_h/dt$ is also applied to both inputs of a multiplier $X_2$ having its output connected to a low-pass filter 53 arranged to produce a voltage $U_{53}$ represented by formula (7). The voltages $U_{52}$ and $U_{53}$ are applied to a divider 54 arranged to produce an output signal $U_{54}$ represented by formula (8). The signals $U_h$ and $U_{54}$ are applied to a multiplier $X_3$, so that the factors A, $\gamma$ and $\lambda$ are not present in the output signal of $X_3$.

Figure 9:
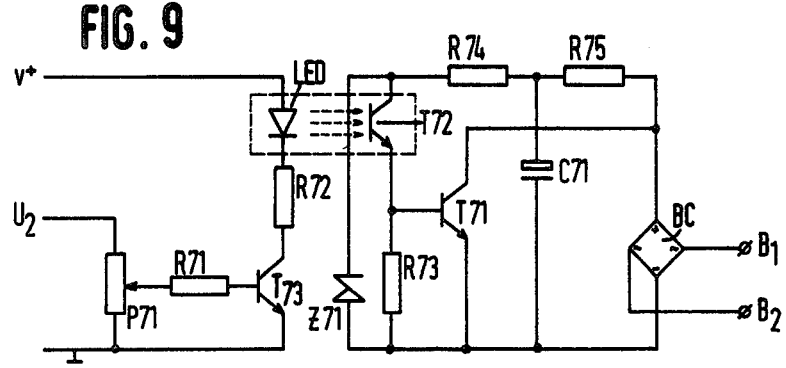
FIG. 9 schematically shows an optical coupling between the pump and the rest of the arrangement.

FIG. 9 shows schematically the optical coupling employed for considerations of safety in the control of the pump. The voltage $U_2$ (see FIG. 7) can be applied through an adjusting potentiometer $P_{71}$ and a resistor $R_{71}$ to the base of a transistor $T_{73}$. The signal produced at the base of $T_{73}$ causes a certain current to flow through a light emitting diode LED. The radiation generated by this LED can impinge upon the base of a light-sensitive transistor $T_{72}$, which produces a current proportional to the incident radiation in the emitter-collector circuit.

The current through $T_{72}$ is amplified by means of a transistor $T_{71}$. The current through $T_{71}$ is generated by a bridge rectifying cell BC. The a-c side of BC is connected to the servo control of pump 58. The number of revolutions of the pump is proportional to the alternating current through the pair of terminals B1 and B2, which is proportional to the current through $T_{71}$.

Although the above describes a typical medical use of the present invention, the present arrangement may, as stated earlier, be applied to all fields in which a fluid level or a particle level, e.g. grain, is to be maintained constant or is to vary in a specific manner.

Various modifications of the present arrangement are feasible without exceeding the scope of the present invention.

We claim:

1. A method of measuring the level of a fluid or other suitable substance contained in a container, comprising the steps of: immersing a detector including at least two electrodes insulated from said fluid or substance in said fluid or substance, coupling said electrodes to a high-frequency voltage supply, and measuring the conductivity of said fluid or substance between said electrodes at a frequency such that the capacitance between each electrode and said fluid or substance is negligible, the impedance of said fluid or substance between said electrodes being indicative of the level of said fluid or substance, the capacitive component of said impedance being negligible at the frequency of said voltage supply.

2. An arrangement for performing the method according to claim 1, characterized by a detector adapted to be immersed in said fluid or substance, said detector including at least two electrodes insulated from said fluid or substance, a high-frequency voltage supply, and a load resistor, one of said electrodes being connected to one terminal of said high-frequency voltage supply and the other of said electrodes being connected to one terminal of said load resistor, the other terminal of said load resistor being connected to the other terminal of said high-frequency voltage supply.

3. A method of controlling the level of a fluid or other suitable substance contained in a container, comprising the steps of: immersing a suction or delivery nozzle connected to a pump and having at least one set of electrodes said nozzle being immersed to said fluid or substance, so that there is no direct contact between said electrodes on the one hand and said fluid or substance and said container on the other hand, generating a voltage proportional to the conductivity of said fluid or substance between said electrodes by means of a high-frequency measuring voltage, multiplying said first-mentioned voltage by said measuring voltage in a synchronous detector and measuring the output voltage of said detector for controlling said pump so that a presettable level is maintained.

4. An arrangement for performing the method according to claim 3, characterized by a suction or delivery nozzle connected to said pump and including at least one set of embedded fully covered electrodes, said nozzle being adapted to be immersed in said fluid or substance, a high-frequency voltage supply, said electrodes being coupled to said high-frequency voltage supply so as to achieve a voltage proportional to the resistance present between said electrodes and means for controlling said pump in response to said voltage so that a predetermined level of said fluid or substance is maintained.

5. An arrangement according to claim 4 including a synchronous detector for multiplying the measuring voltage by the voltage measured, a proportional controller connected to the output of said synchronous detector for setting a desired level, said controller being adapted to produce a controlled output voltage, a differentiator adapted to produce a differentiated voltage of said controlled output voltage, a first multiplier for forming the product of said differentiated voltage and a pump control voltage, a low-pass filter adapted to produce a first voltage and having its input connected to the output of said first multiplier, a second multiplier for multiplying said differentiated voltage by itself, a second low-pass filter having its input connected to said second mulitiplier and adapted to produce an output voltage, a divider for forming the quotient of the output voltages of said first low-pass filter and said second low-pass filter, and a third multiplier for forming the product of said quotient and said controlled output voltage.

6. An arrangement according to claim 4 including an accelleration limiter for limiting the over- or underpressure in said nozzle as caused by pump action.

7. An arrangement according to any one of claims 4, including two transformers, said electrodes being floatingly connected between said two transformers.

8. An arrangement according to claim 4, including a light emitting diode and a light-sensitive transistor, said pump control voltage serving for pump control being applied to said pump by means of said light emitting diode and said light-sensitive transistor.

9. A method according to claim 3 wherein said nozzle includes at least one set of fully embedded and fully covered electrodes peripherally spaced along the wall enclosing a central aperture, said nozzle further including lead wires for said electrodes.

10. A method according to claim 3 for eliminating the infuence of the surface area of said fluid or substance, differentiating an output voltage produced by said controller, multiplying to a proportional controller by means of which a desired level can be set said differentiated voltage by a pump control voltage to be used for pump control, passing the product voltage through a low-pass filter to produce a first voltage, dividing said product voltage by the product of the differential voltage multiplied by itself said second product voltage through a low-pass filter to produce a second voltage, multiplying the output voltage by a quotient voltage so as to form the pump control voltage for controlling the pump.

* * * * *